US008162295B2

(12) United States Patent
Mou

(10) Patent No.: US 8,162,295 B2
(45) Date of Patent: Apr. 24, 2012

(54) REACTION VESSEL ASSEMBLY WITH GAS EXCHANGE MEANS

(76) Inventor: Duen Gang Mou, Taipei (TW)

( * ) Notice: Subject to any disclaimer, the term of this patent is extended or adjusted under 35 U.S.C. 154(b) by 904 days.

(21) Appl. No.: 12/202,433

(22) Filed: Sep. 2, 2008

(65) Prior Publication Data

US 2009/0152744 A1  Jun. 18, 2009

(30) Foreign Application Priority Data

Dec. 17, 2007 (TW) .............................. 96148229 A

(51) Int. Cl.
  *B01F 3/04* (2006.01)
(52) U.S. Cl. ........................................ 261/84; 261/119.1
(58) Field of Classification Search .................. 261/84, 261/119.1
  See application file for complete search history.

(56) References Cited

U.S. PATENT DOCUMENTS

| 2,465,811 | A | * | 3/1949 | McQuain | 215/283 |
| 5,443,985 | A | * | 8/1995 | Lu et al. | 435/393 |
| 5,895,211 | A | * | 4/1999 | McMillan | 431/10 |
| 6,017,761 | A | * | 1/2000 | Rigg et al. | 435/455 |
| 2004/0004717 | A1 | * | 1/2004 | Reed | 356/338 |
| 2005/0186669 | A1 | * | 8/2005 | Ho et al. | 435/287.1 |
| 2006/0019385 | A1 | * | 1/2006 | Smith et al. | 435/348 |

* cited by examiner

Primary Examiner — Robert J Hill, Jr.
Assistant Examiner — Christopher P Jones
(74) Attorney, Agent, or Firm — Pai Patent & Trademark Law Firm; Chao-Chang David Pai

(57) ABSTRACT

A reaction vessel assembly achieves enhanced aeration or gas exchange in its gas-in-liquid multiphase mixing reaction through the use of its mixing energy and gas-lift venting, and without the traditionally practiced external line gas sparging. It combines the best of both shake flask and stirred tank reactor vessel and possesses some of the key generic features like cost and parallel experiment advantages of the traditional flasks and shaker hybrid but without their shortcomings like limited gas exchange and uncharacteristic mixing.

17 Claims, 7 Drawing Sheets

REACTION VESSEL ASSEMBLY WITH GAS EXCHANGE MEANS

BACKGROUND OF THE INVENTION

Incubating shakers are used to serve reaction flasks and their content in providing desired temperature, stirring, mixing and resulting gas-to-liquid mass transfer through either rotary or reciprocating shaking motion for nearly half a century. Both have throw motions normally in range of 12.5 to 50 mm, i.e., 0.5-2 in, the maximum linear distance moved by any point in and on the flask. Reciprocation is usually about 100 cycles/min and in rotary shaking the range is about 150 to 300 rev/min (Pirt, 1975). The mechanical drive and shaft mechanism causes the shaker table and flask vessels clamped on to the table to gyrate, orbit or move thereby causing the shaker table and flask vessels to shake. When used in microbial fermentation industry, for example, the objectives are usually two folds. One is to provide the key link in translating laboratory culture data to commercial scale operation, i.e., scale up; and the other in scaling down environmental conditions achievable in commercial scale equipment to this laboratory and frequently bench size equipment. Both are to insure that improvement studies are carried out under conditions that can be duplicated in either direction. (Aiba, Humphrey and Millis, 1973)

Shaken flasks' main utility is in the comprehensive change of reaction conditions from one flask to another and/or from one incubating shaker to another, e.g., substrate concentration, temperature, reacting species/formulation, mixing power, etc. The simplicity of its preparation and operation, and the economy in time, material, flask acquisition, and hence number advantage for repeated runs have made shaken flask a work horse and its unshaken generic role in science and engineering labs. (Betts and Baganz, 2006; Kumar, Wittmann and Heinzle, 2004)

One well known drawback of shaken flask (often conical Erlenmeyer flasks) is its limited atmospheric gas exchange or ventilation when reaction must be shielded from the ambient to avoid contamination, notably the use of cotton or sponge plug or gauze/cotton/gauze "sandwiched" layers for closuring from air-born contaminants when culturing things like microbes. Here, atmospheric exchange between flask headspace and ambient incubator gas is limited to natural convection or diffusion resulting from concentration gradient across the porous gas-diffusible closuring. Blocked by the porous or spongy closure, gaseous reaction product tends to get concentrated in flask headspace, while feeder or substrate gas stayed out. In aerobic microbial culture this may result in reduced cell growth and the consequent reaction rate due to oxygen starvation and/or $CO_2$ inhibition. The same is true with the openings, closuring or caps of other static and/or shake culture vessels such as test tubes, tissue culture T-flasks, micro-titer plate, etc. (Betts and Baganz, 2006; Kumar, Wittmann and Heinzle, 2004).

This becomes less a problem when larger and more sophisticated reaction vessels like standard stirred tank reactor (STR) are used. They solve this gas exchange or ventilation problem by forced ventilation such as use of direct sparging, membrane permeation, reaction chamber pressurization, gas pumping, etc. to supply the substrate gas, and in turn purge the waste or product gas out of the vessel. During direct gas sparging in a standard STR, substrate-gas bubbles are injected toward and chopped and dispersed by the high speed impeller blades. The resulting fine gas bubbles not only increase the volume of gas holdup in the liquid phase, but also provide expanded gas-liquid interfacial area for enhanced gas transfer into solution. Forced ventilation or gas sparging using pressurized line gas supplies fresh feeder gas and purges inhibitory waste product gas like oxygen and $CO_2$, respectively, inside a microbial culture vessel, to facilitate higher rate of reaction such as faster aerobic cell growth.

However, forced ventilation, using pressurized line gas, on smaller size reaction vessel like shaken flask is not easily workable without compromising its aforementioned advantage of simplicity and economy in time, material, acquisition, and number. Hence, gas supply, exchange or ventilation in enclosed reaction vessels like flasks, bottles, beakers, tubes, micro-titer plate wells, etc. (they are all termed "reaction vessel" below) in number in floor or bench-top scale shaker or mixer is still without a solution which can combine the best of shaken flask and STR. Available solutions in tissue cell and/or microbial culture see modifications of vessel closuring cap for sterile venting and breathing of tissue culture flask (TPP/MIDSCI Tissue Culture Products from BD Falcon; Eudailey and Lyman, 2007), of tissue culture flask compartmentalization for better maintenance of high cell density (Wilson and Wolf, 1997), of microbial fermentation flasks' shape and locations of their membraned "windows" for gas exchange capacity (Kato and Tanaka, 1998), of improved microbial flask baffling and closuring for enhanced aeration (Tunac, 1987), of system for sparged aeration of six 500 ml microbial flasks on shaker (Donovan, Robinson and Glick, 1995), of gas delivering fittings on tissue culture spinner flask for forced gas supply and aeration (ProCulture Spinner Flasks from Corning), and of single-use hybrid-mode bag bioreactor using sparge tube and stirring propellers for STR-like mixing and aeration (CellMaker PLUS from Cellexus Biosystems). These improvements all but still rely basically on either natural convection thru the vessel closurings like the shake flask or forced gas flow by sparging like the STR. The patent literature by Tunac (1987) and journal article by Kato and Tanaka (1998) in particular addressed the same problem as this invention, but only went as far as with shaker-motion-enhanced local gas "disturbance" in and around the modified venting cap or the membraned "windows" of the flask, and without the sustained and controlled fresh gas supply and purging within and the quantitative proof emphasized in present invention.

Extensive search of patents, scientific journals and Internet content databases reveal no prior design, use or application meeting the functional criteria of sustained convective flow of fresh gas intake and spent gas vent with aid of indigenous liquid mixing and without use of line gas in present invention. Known laboratory shake flask, incubator shaker and bioreactor suppliers also do not carry product meeting these criteria. Recent reviews of relevant prior art were authored by Betts and Baganz (2006) on miniature bioreactors and by Kumar, Wittmann and Heinzle (2004) on minibioreactors.

BRIEF SUMMARY OF THE INVENTION

Present invention reveals an assembly of a reaction vessel enclosure which has at least a liquid phase, a gas phase and partitions of essentially an interconnecting gas intake compartment and a gas venting compartment. With help of the reaction vessel's indigenous mixing power, this assembly allows steady and measureable fresh gas flow into the gas intake compartment and then into the reaction liquid phase before venting to vessel ambient thru the gas venting compartment without an external pressure means.

In one aspect of the present invention, the reaction vessel enclosure includes two separate openings and a mixing motion drive device. One opening connects the gas intake compartment to vessel ambient and allows fresh gas intake from the ambient into the reaction chamber and then pumped as gas bubbles into the reaction fluid mix by the mixing motion drive device. The entrapped gas bubbles in turn vent thru the other opening which connects the gas venting compartment to vessel ambient. The mixing motion drive device can be hand or machine powered. Machine power can come thru a partially or totally submerged impeller or a magnetic stirring bar internal to the reaction vessel, or thru an external shaker table.

In another aspect of the present invention, a small motor is used to drive the mixing impeller which in turn pumps the fresh gas intake into the reaction fluid. To aid power drawn and reduce vortex formation, impeller rotation axis can be at the vessel center axis of symmetry or off-center from the vessel center axis of symmetry, and it can be parallel to the vessel center axis of symmetry or not parallel to the vessel center axis of symmetry.

In still another aspect of the present invention, inside the reaction chamber the vessel can have one or more baffle plates to aid the mixing power drawn and the pumping or entrapment of gas into liquid.

The gas so entrapped in the reaction fluid inside the reaction chamber is vented, in one aspect of the present invention, through the interconnecting gas venting compartment and its opening to the ambient. The gas venting compartment, shielded from the bulk fluid mixing motion in the interconnecting gas intake compartment, works like a gas-lift riser tube or column and allows entrapped gas bubbles entering from the tube's submerged end to vent by floatation force to vessel ambient thru the other end. This steady but significant convective gas vent or out-flow creates a negative pressure differential between the interconnecting gas intake compartment and vessel ambient. This negative pressure differential in turn results in more fresh convective gas intake from vessel ambient into the reaction chamber. This perpetual cycle of gas pumping and venting continues as long as the mixing motion and gas entrapment power on and sufficient pressure differential overcomes resistance at the gas intake as well as the gas vent ports.

In yet another aspect of the present invention, the gas-lift riser tube is used both as the venting compartment and a vortex-breaking baffle for, respectively, enhanced convective gassing flow and mixing power drawn. This is made possible thru impeller pumping of headspace gas into the liquid and the guided escape of entrapped gas bubbles thru the gas-lift riser tube. The bigger the opening or cross-sectional area at the immersed end of the riser tube and the higher the volume of liquid gas holdup become, the more the convective gas flow or ventilation between the vessel and ambient. This kind of gas pumping by mixing is not possible with traditional shaken flask due to its non-compartmental configuration and working principle.

In still another aspect of the present invention, the reaction vessel can be configured in forms of tube, flask, bottle, beaker and tubing and can be in materials of glass, plastic and metal. The reaction may involve any physical, chemical and biological mixing reaction employing multiple-phase gas and liquid substrates and products.

In yet another aspect of the present invention, mass produced and commercially available off-the-shelf wide neck glass bottle, like the 80 mm diameter neck size bottles in six different sizes from 0.5 to 20 liter made by Schott Duran GLS 80, is used as main body of the stirred reaction vessel much like the traditional hybrid of the glass shaken flask and its externally powered shaker.

In still another aspect of the present invention, when used as bundled reaction vessel array like traditional shaken flasks on a shaker table, unlike shaken flask incubator which ties all flasks to one shaker table and must stop all flasks for sampling even a single flask and is often shared among lab personals, each stirred reaction vessel in the bundle can be run independently from one another, having its own stirring speed and/or reaction temperature selections, and can be sampled without stopping the stirring motor. This new freedom has added advantage in experiment design and energy efficiency (vs. vacant spaces on a heavy shaker table). Furthermore, unlike shaken flask incubators, individual convenience and group access are no longer conflicting objectives.

Present invention of a reaction vessel assembly combines the best of both shaken flask and STR vessel but without flask's shortcomings of limited gas exchange capacity. A complete invention description is not limited to what shown and described but is susceptible to modifications and changes known to one of ordinary skill in the art.

DETAILED DESCRIPTION OF THE INVENTION

1. Reaction Vessel Assembly and its Operation

Figure 1A:
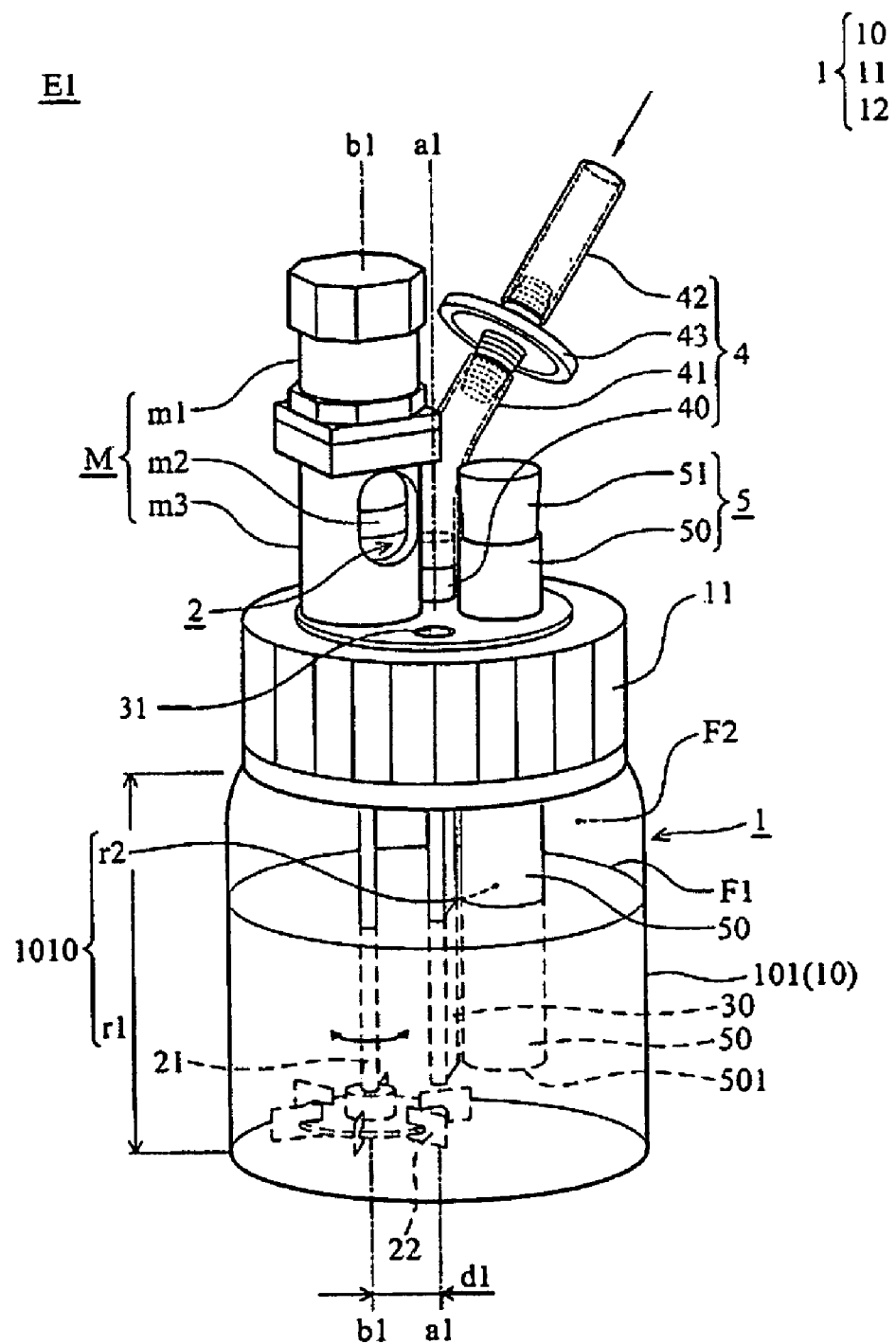
FIG. 1A is a perspective view of the new reaction vessel assembly in accordance with a preferred embodiment of the present invention, comprising a top-mounted stirrer with a small detachable motor, a filtered gas intake, a gas-lift vent and a baffle plate for enhanced mixing.
Figure 1B:
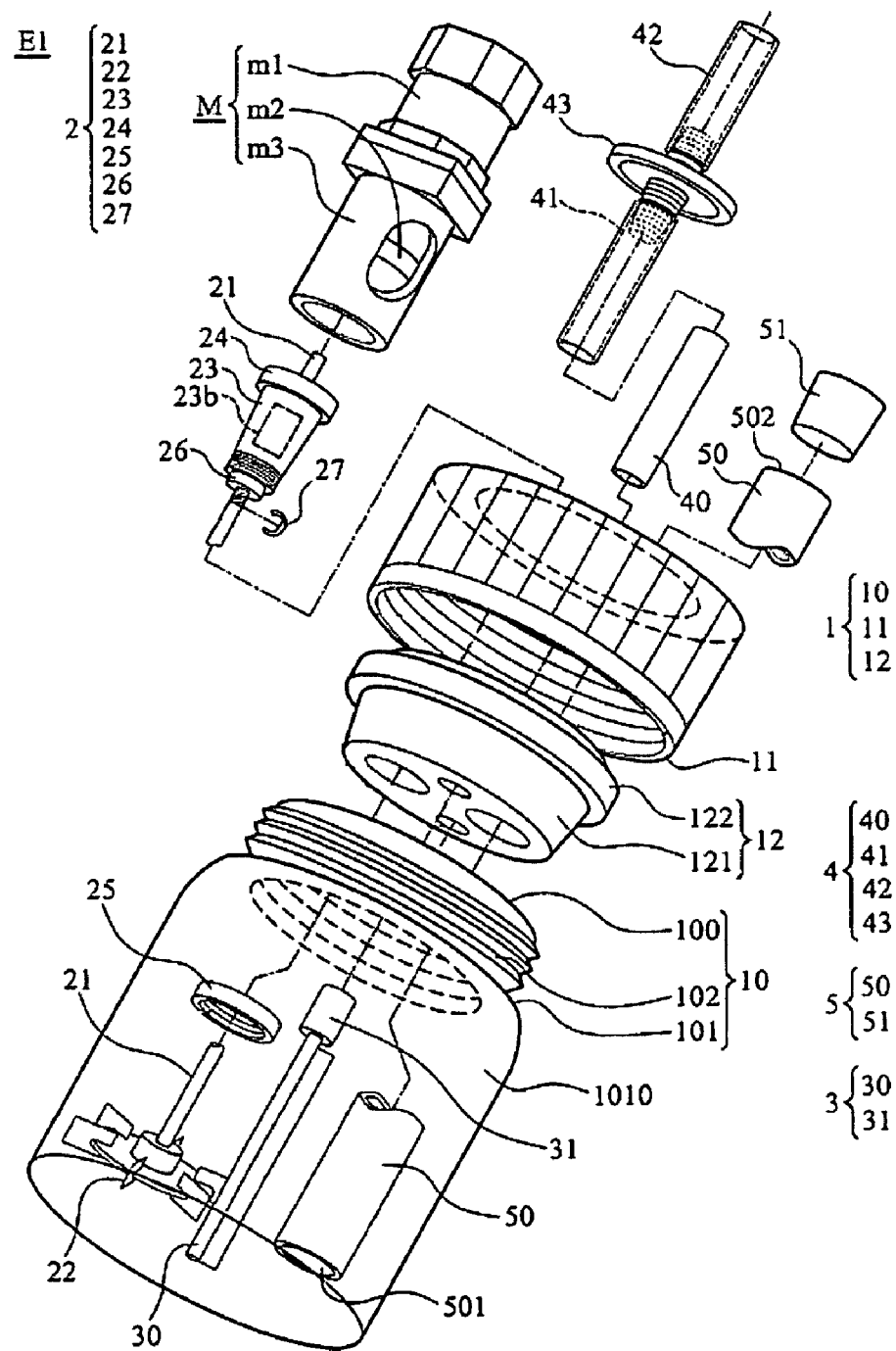
FIG. 1B is an exploded view of the new reaction vessel assembly shown in FIG. 1A.

FIG. 1A and FIG. 1B illustrate one three-dimensional view of an embodiment of the reaction vessel assembly E1 (with liquid content F1) of the present invention. The reaction vessel assembly E1 comprises a mixing motion drive assembly M, a vessel enclosure 1, a motion transmission assembly 2, a baffle plate assembly 3, a gas intake assembly 4, and a gas vent assembly 5.

The mixing motion drive assembly M includes a motor m1, a shaft coupling m2 and a quick-connect housing m3. The motor m1 is connected to the vessel enclosure 1 through the quick-connect housing m3. For the motor m1, commercially available small palm-size 12-24V DC motors with or without carbon brush may be used. Their speed is adjustable with reducing gear box and variable DC volt input, also available commercially.

The vessel enclosure 1 includes a vessel main body 10, a vessel closure locking cap 11 and a head plate stopper 12, with the head plate stopper 12 capped by the vessel closure locking cap 11 to form an air tight seal on the vessel main body 10. The motion transmission assembly 2, the baffle plate assembly 3, the gas intake assembly 4, and the gas vent assembly 5 are all anchored to the vessel enclosure 1 by mounting onto the head plate stopper 12.

The vessel main body 10 is a container like a glass beaker, flask, bottle or carboy which has a threaded opening large enough to accommodate the head plate stopper 12 with all its mounted assemblies, and a head plate stopper 12 fastening means like the threaded locking cap 11 and the matching vessel opening neck 102. The vessel main body 10 also contains a reaction chamber 1010 inside the vessel body 101 which encloses at least a liquid phase F1 and a gas phase F2, which is connected to the ambient through the gas intake assembly 4 and the gas vent assembly 5 on the head plate stopper 12. The reaction chamber 1010 has a center axis of symmetry a1-a1 perpendicular to its bottom plane. The reaction chamber 1010 includes two interconnecting compartmentalized spaces, a gas intake space r1 and a gas vent space r2. The gas intake space r1 is essentially the entire space in and above the liquid phase F1 inside the vessel main body 10 stirred by the motion transmission assembly 2, excluding the gas vent space r2 confined inside the gas vent assembly 5. Both the gas intake space r1 and the gas vent space r2 are regions containing multi-phase reaction mixture of at least one liquid and one gas phase. It's worth mentioning that for the vessel main body 10, one off-the-shelf commercial lab glassware may be used—the wide 80 mm neck size GLS 60 Series glass bottle with six different size selections from 0.5 to 20 liter made by Schott Duran, Germany. Other size and shape vessels may also be used if they can be matched and configured accordingly.

The head plate stopper 12's air tight seal is assured by an extended ring-flange 122 which forms an air tight seal on the rim of the vessel opening 100 when pressed down by the threaded locking cap 11 and locked tight by screwing 11 onto the vessel neck 102. The head plate stopper 12 uses a plurality of ports for component inserts. The head plate stopper 12 may be molded or machined using one piece rubber or plastic respectively. When made from hard plastic, the extended ring-flange 122 uses a rubber o-ring at its underside (not shown) to achieve air tight seal. When made from rubber, mass and thickness of the tapered part of the head plate stopper 121 is important for mechanical stability of the motion transmission assembly 2.

The motion transmission assembly 2 connects the motor m1 to a stirring device and through it provides power for mixing between the liquid phase F1 and the gas phase F2 within the reaction chamber 1010. The motion transmission assembly 2 comprises a stirrer shaft 21, a multi-blade impeller 22, a bearing assembly 23b, a conical shaped bearing housing 23 with a top locking ring nut 24 on its top and a bottom locking ring nut 25, a spring-loaded mechanical seal 26, and an E-shaped spring clip 27 for its anchoring. The top and bottom ring nuts 24 and 25 and the conical shaped bearing housing 23 are used to stabilize and secure the motion transmission assembly 2 onto the head plate stopper 12.

The bearing assembly 23b provides axle direction (i.e., b1-b1) stability to the rotating stirrer shaft 21 and is held inside the bearing housing 23. This axle direction b1-b1 of the stirrer shaft 21 can be placed along the central axis of symmetry a1-a1 of the reaction chamber 1010. It can also be placed as illustrated in FIG. 1A with an offset d1 from the central axis a1-a1 for lower vortex and better mixing. It can run parallel to a1-a1 as illustrated in FIG. 1A, or it can run with an angle to a1-a1 again for better mixing effect. The main objective in placing b1-b1 is to suppress vortex and maximize gas bubble entrapment or gas holdup.

The impeller 22 is of the design suitable for gas entrapment and may include many of the popular types like marine, paddle, vaned, Rushton, etc. Their geometry and rotation speed are factors closely associated to gas-liquid mixing/pumping efficiency.

In lower reaction volume applications, table top magnetic stirrer coupled with a stirring bar inside the reaction chamber 1010 can also be used for gas entrapment and pumping in place of the above illustrated mixing motion drive assembly M and the motion transmission assembly 2.

The baffle plate assembly 3 uses one or multiple baffle plates 30 (with one shown) can either be secured at an insertion port 31 onto the head plate stopper 12 as shown in FIG. 1B or be welded or attached to other immersed objects anchored to the head plate stopper 12 like the gas vent assembly 5 or a thermometer well (not shown) or be a fixture as part of the reaction chamber 1010. Standard baffle design considerations like those in standard STR vessels are applicable here in breaking vortex and managing mixing power drawn. This also includes design and user adjustment of all immersion objects' projected cross-section area/profile perpendicular to the fluid flow. Given all that, the baffle plate aids but is not essential to the practice of gas pumping in this invention.

The gas intake assembly 4 uses a filter 43 to keep off contamination and is connected to the reaction chamber 1010 through the head plate stopper 12 using flexible tubing pieces 41, 42 and a hard tubing insertion port 40. In this embodiment of this invention, the filter 43 uses a pre-fab 0.2 micrometer membrane filter to keep away micro contaminants. Traditional cotton or glass wool filter can also be used for this purpose.

Figure 2:
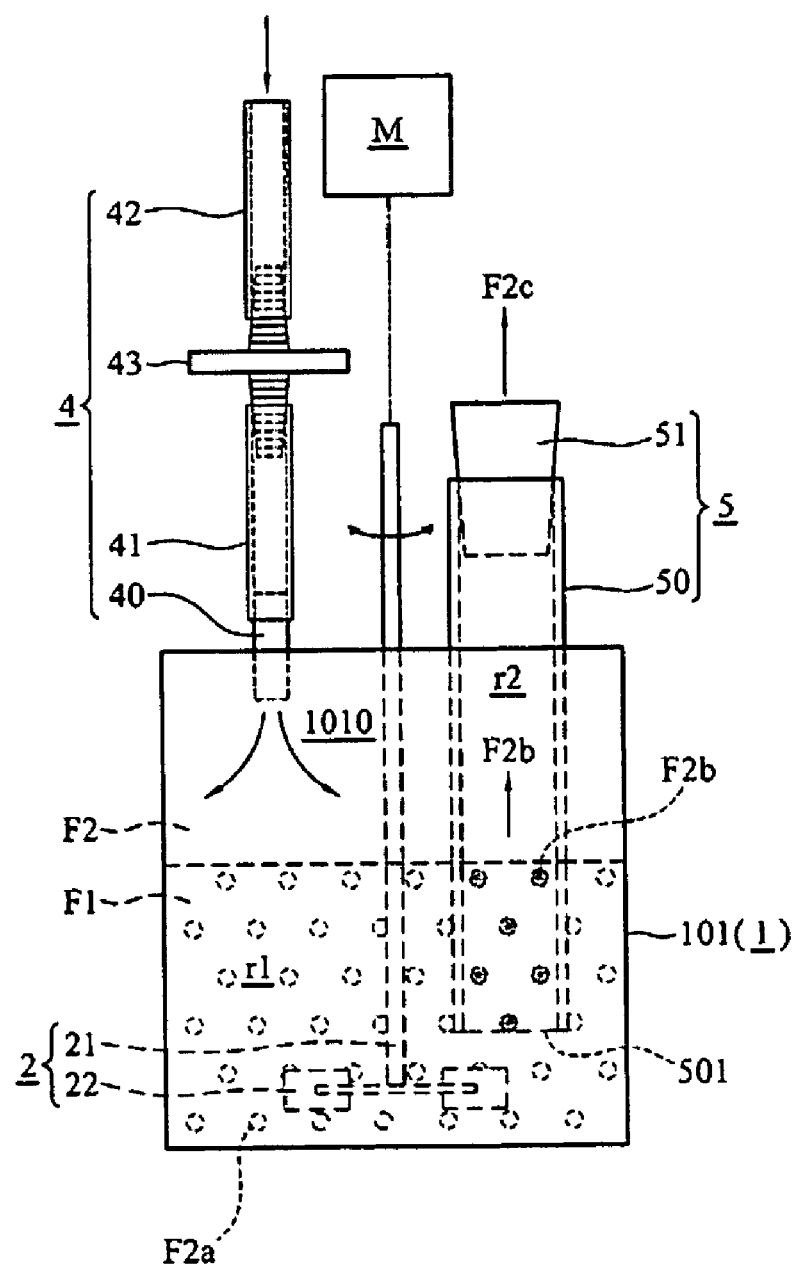
FIG. 2 shows a working schematic of convective flow of fresh gas intake and spent gas vent in the new reaction vessel assembly: from filtered gas intake to gas entrapment and pumping by the in situ stirring impeller to guided gas bubbles escape through the immersed end of the gas-lift venting tube.

The gas vent assembly 5 starts with a gas-lift venting tube 50 and ends at a crack-opened test tube cap (not shown) or, if sterility in the chamber 1010 is a must, a porous sponge plug 51 at its opening to the ambient. The gas-lift venting tube 50 works as a shielded gas lift riser tube and allows entrapped gas bubbles in the liquid to escape by floatation to the ambient. In this embodiment of the invention, the gas vent compartment uses a 360 degree partition—a round gas-lift tube 50—with an opening 501 to the liquid and an opening 502 to the ambient. Its main function is to shield a portion of the entrapped gas bubbles from mixing disturbance in the reaction chamber 1010 in order for them to vent freely using its gas-lift momentum (as is illustrated in FIG. 2). Vent opening 502 also allows convenient sampling of the liquid content by hand or a robot arm without disturbing the liquid mixing and the gas exchange.

As shown in FIG. 1A, after the motion transmission assembly 2, the baffle plate assembly 3, the gas intake assembly 4 and the gas-lift vent assembly 5 are mounted to the head plate stopper 12 and the head plate stopper 12 is pressed and locked onto the vessel opening 100, the stirring impeller 22, the baffle plate(s) 30 and the gas-lift venting tube 50 are hence suspended inside the vessel and at the same time submerged inside the reaction fluid F1 in the reaction chamber 1010.

Reaction vessel assembly E1 is unique in providing convective flow of fresh gas intake into the headspace F2 and the reaction chamber 1010's gas intake space r1 and spent gas vent thru reaction chamber 1010's gas vent space r2 to the ambient with aid of the mixing power and without the use of line gas or pressure. Mixing reaction in this illustration is suitable for, but not limited to, microbial fermentation. It is equally applicable to other gas-liquid multi-phase physical, chemical and biological mixing reactions limited by feed or substrate gas availability.

Figure 3:
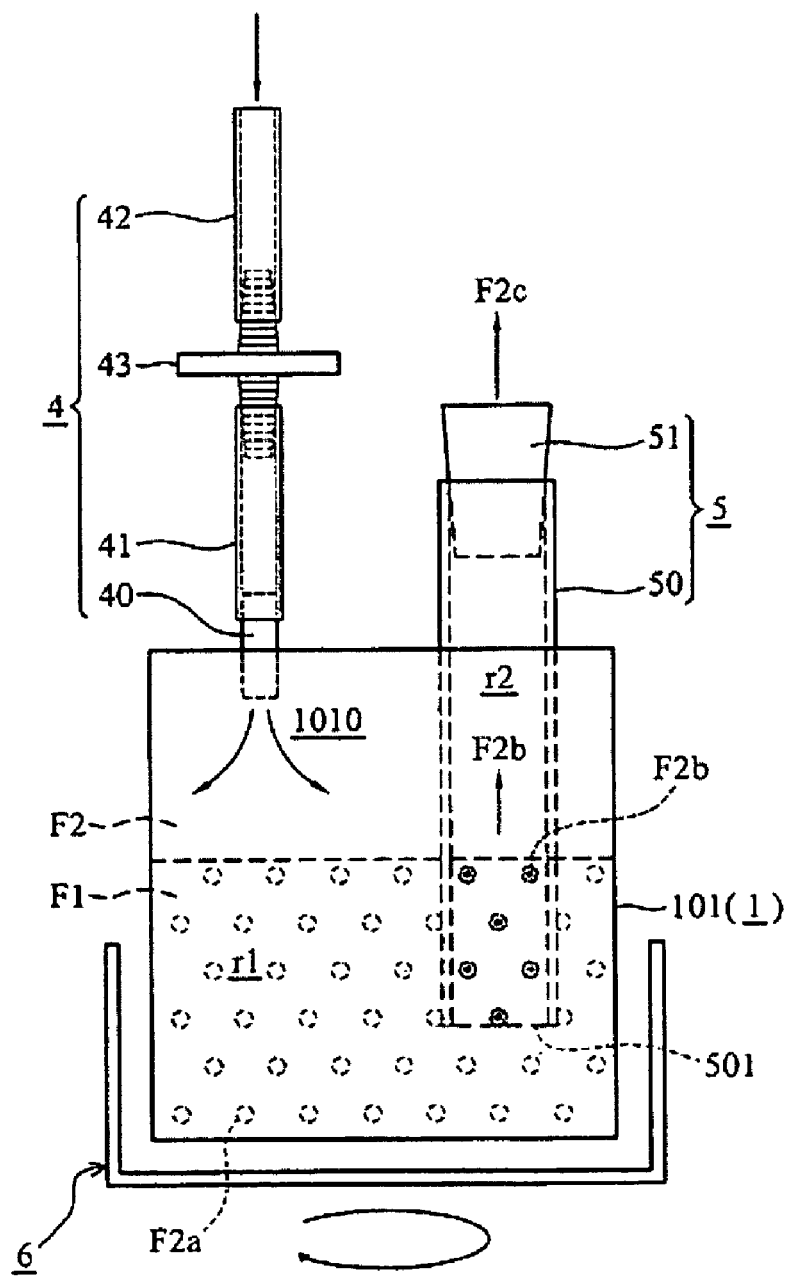
FIG. 3 shows the same working schematic of convective flow of fresh gas intake and spent gas vent in the new reaction vessel assembly as FIG. 2 but using the stirring or mixing power instead from an external source, such as hand swiveling or a shaker table.

This convective flow takes place in the sequence of fresh gas intake from the ambient thru the gas intake assembly 4 into the reaction chamber 1010's headspace F2 and then the blending of intake gas into the reaction liquid phase F1 in forms of fine gas bubbles F2a and F2b by the mixing power from the impeller 22 driven by the mixing motion drive assembly M as shown in FIG. 2 or from a swiveling hand or a shaker table 6 as shown in FIG. 3. The gas bubbles trapped inside the shielded gas vent space (r2) or the gas-lift venting tube 50, denoted F2b, can then escape from the liquid phase F1 to the ambient thru the the gas-lift venting tube 50 and the sponge plug 51. Due to the air-tight vessel head plate, this convective gas vent F2c to the ambient creates a negative pressure differential between the interconnecting gas intake space r1 inside the reaction chamber 1010 and the vessel ambient. This negative pressure differential in turn sucks in more fresh gas from vessel ambient into the vessel headspace F2 in amount proportional to gas vent flux F2c. This cycle of gas pumping and venting continues as long as the mixing motion and gas entrapment move on and sufficient pressure differential overcomes resistance at the gas intake as well as the gas vent ports.

To show how the new reaction vessel assembly works, FIG. 2 and FIG. 3 give a schematic view of the reaction vessel assembly E1 shown in FIG. 1A. They display the vessel enclosure unit 1, mixing motion drive assembly M and transmission assembly 2 or shaker table 6, gas intake assembly 4 and gas vent assembly 5. They show how floatation-force-lifted entrapped gas bubbles F2a, once caught inside the partially submerged gas-lift venting tube 50, become venting gas bubbles F2b, which end up in gas vent space r2 before escaping as spent gas vent flux F2c to the ambient.

2. Reaction Vessel Assembly Array Bundle

Figure 4:
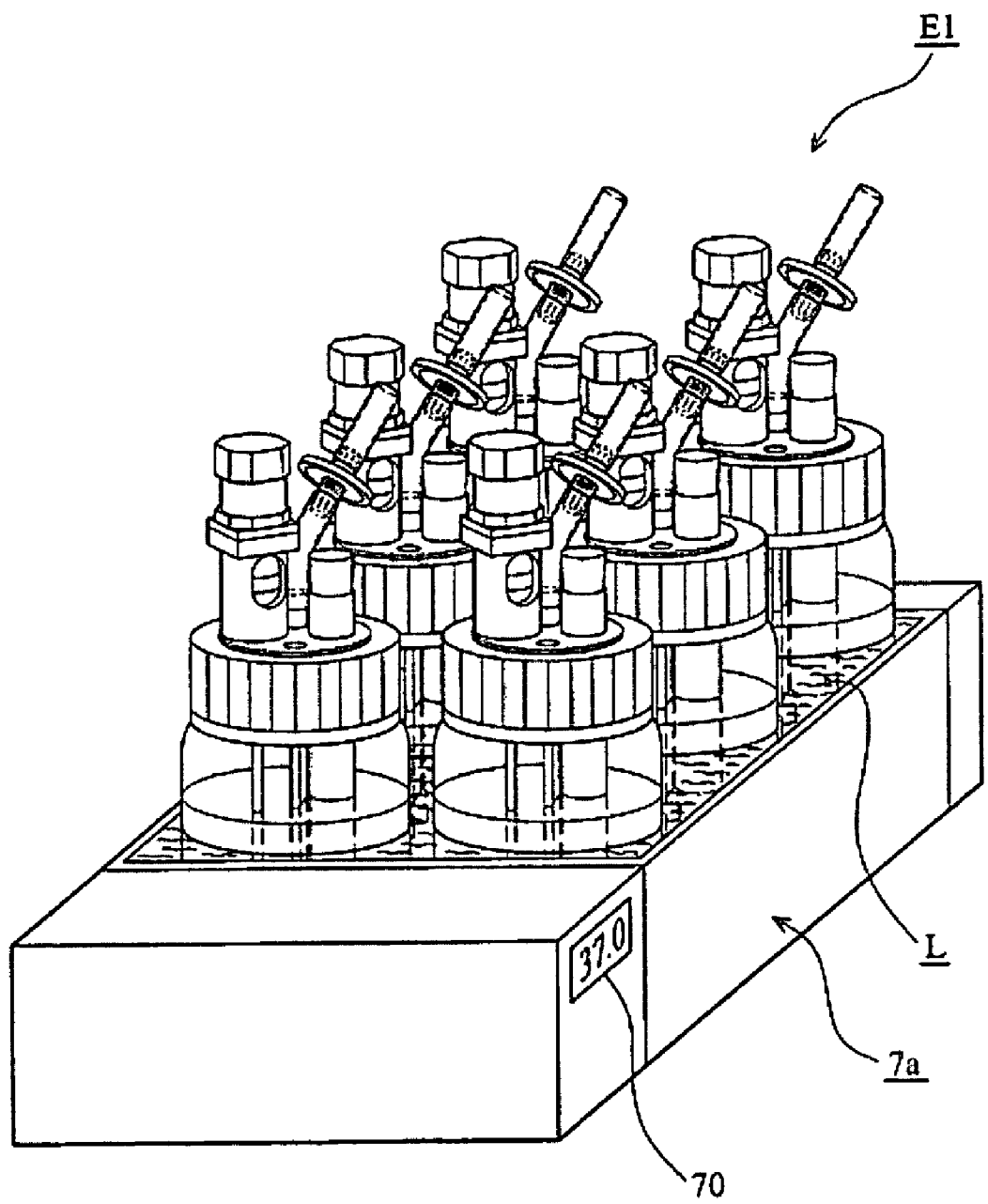
FIG. 4 illustrates one way to run the new reaction vessel assembly array in an incubating water bath.
Figure 5:
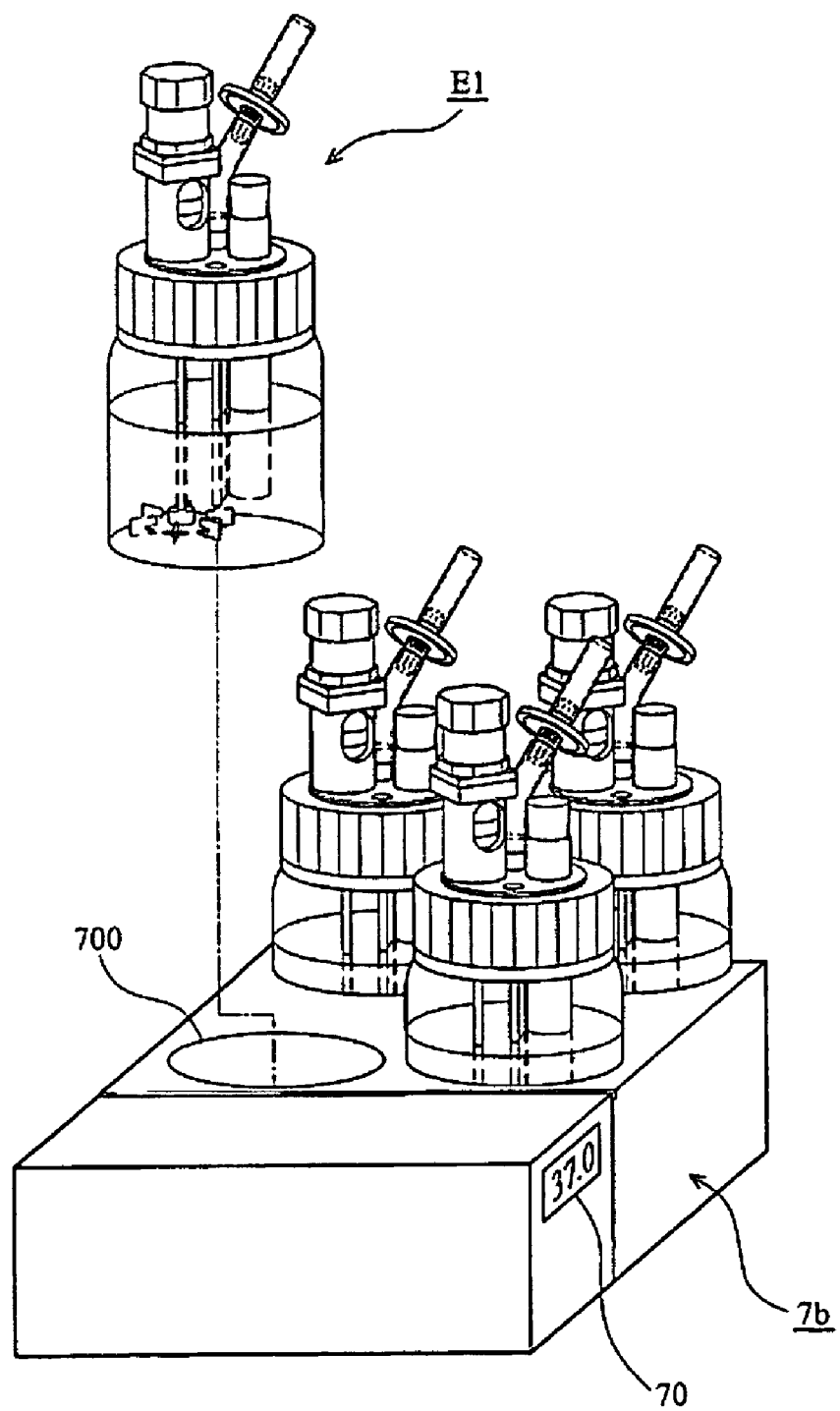
FIG. 5 illustrates one way to run the new reaction vessel assembly array on an incubating dry bath or hot plate with single or multiple thermostat-controlled temperature zones.

FIG. 4 and FIG. 5 show, like generic flasks-and-shaker hybrid, how the present stirred reaction vessel assembly E1 with the new aeration enhancing means can conveniently be incubated in constant temperature (70) lab water bath 7a or dry bath/hot-plate 7b in plural number for mixing reaction study in the lab. Water bath incubator is known for its superior temperature uniformity and stability, while constant temperature dry bath/hot-plate incubator for its being free of water L splashing hazard. Just like generic flasks-and-shaker hybrid, larger number parallel experiment bundles can certainly use a plurality of such lab incubators or a walk-in incubation room for reaction temperature control. Dry bath/hot-plate 7b with multiple thermostated-temperature zones 700 has added convenience of simultaneous reaction temperature and mixing condition screening. This cannot conveniently be done with traditional flasks-and-shaker hybrid with only one shaker table. The in situ mixing impeller also allows non-interrupted stirring when sampling content of the new reaction vessel assembly. This, likewise, is not possible with traditional flask shakers—all flasks must stand still with the shaker table turned off when sample even a single flask. In addition, with a more favorable content-to-vessel-footprint ratio, the new stirred reaction vessel array also uses far less floor or bench space per unit volume of reaction preparation when compared to traditional conical-shaped flask shaker incubator.

3. Quantitative Measurement of Gas Flow in Reaction Vessel Assembly

Figure 6:
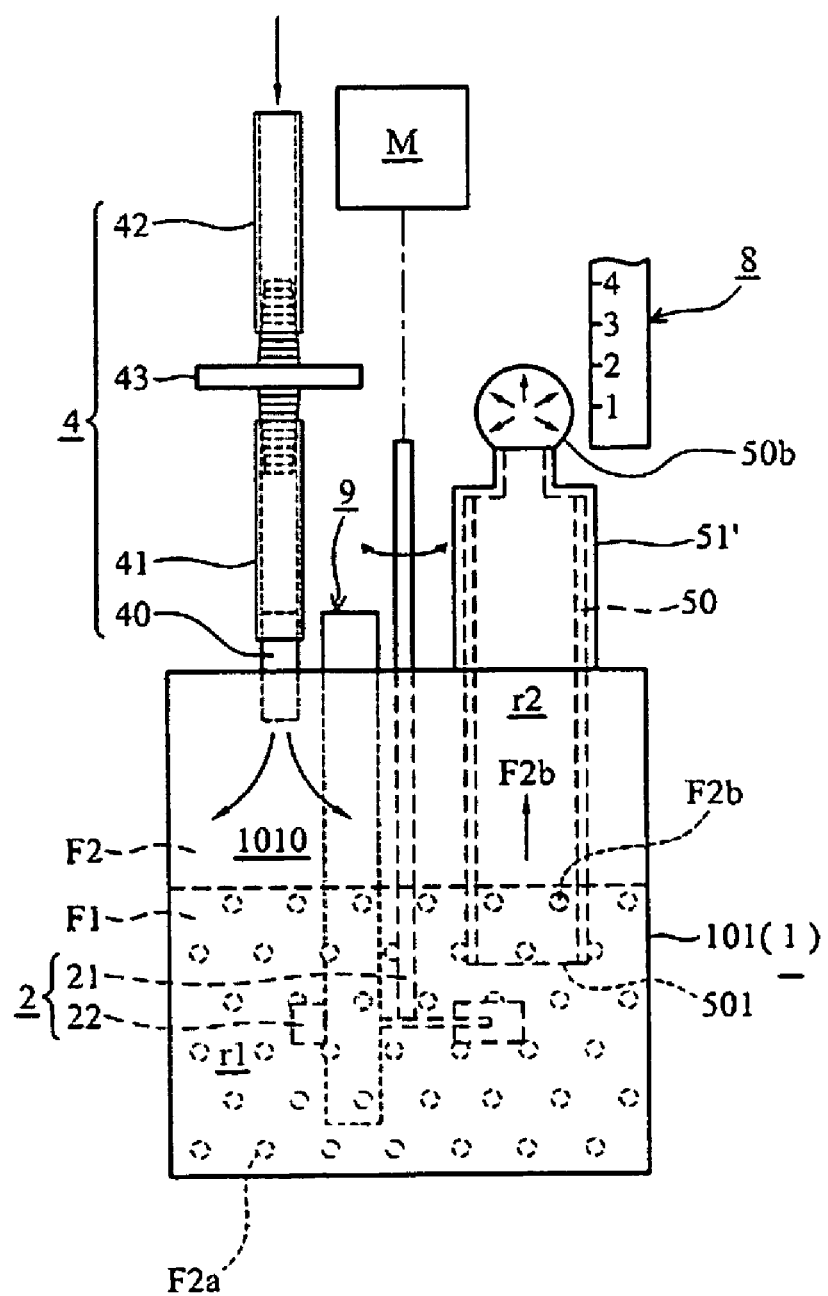
FIG. 6 is a schematic of the soap bubble experiment setup for quantitative measurement of the convective flow of fresh gas intake and spent gas vent.

FIG. 6 shows a schematic of the reaction vessel assembly E1' used for quantitative measurement of convection gas flow rate in the present invention. The reaction vessel assembly E1' has one thermometer well 9 in place of the baffle plate 30 shown in FIG. 1A/1B. The measurement method, calculation and actual gas flow rate data are described in the EXAMPLE Section below. Under ambient and atmospheric condition, air flow or aeration rate is the volumetric gas flow rate measured.

EXAMPLE

Dimensions of a 500 ml Schott Duran GLS80 reaction vessel assembly E1' in FIG. 6 are the following: the gas inlet port insert 40 and the thermometer well 9's OD and ID, respectively, 8 and 6 mm; the gas-lift venting tube 50's OD and ID, respectively, 20 and 17 mm; 6-blade impeller 22's diameter and height, respectively, 38 and 10 mm; tap water volume in reaction chamber 1010 400 ml. The liquid phase F1 is 58 mm in depth, the submersion depth of thermometer well 9, the gas-lift venting tube 50 and the impeller 22 are, respectively, 42, 22 and 32 mm. To make a blow-hole for soap bubble 50b blowing measurement, a rubber material 16 mm serum tube plug 51' was pulled inside out and the plug end bored open and placed on top of the opening of the gas-lift venting tube 50. This produces an 8.5 mm ID blowhole for the soap bubble blowing experiment and is used to measure the gas vent flux by timing and measuring the bursting height or diameter of the soap bubble 50b from a finger smear of soapy water over the blowhole on top of the gas-lift venting tube 50 at time zero.

One to 2 ml of olive cooking oil is added to tap water liquid phase F1 inside the reaction chamber 1010 to collapse the soapy foam accumulated inside the gas-lift venting tube 50 after many repeated bubble blowing experiments over long measurement sessions. The size of soap bubble 50b in millimeters diameter before bursting was read with a millimeter ruler 8 placed next to the blowhole and recorded together with the time it took the bubble to burst in seconds. With a little practice, it is possible to get consistent measurements at burst of the size of the soap bubble 50b and the time it takes at different impeller 22 speeds. Volume of bubble, V, is calculated from the bubble diameter before bursting, D, as $V=\pi D^3/6$. Intake gas flux into the vessel headspace F2 in milliliter air per minute (ml/min) is obtained by further dividing the bubble volume V before bursting by the time it takes the bubble to burst in seconds. TABLE 1 below lists measurements with a 50 mm diameter pre-fabricated disc membrane filter 43 of $0.2\mu$ pore installed on the gas inlet port insert 40:

TABLE 1

Reaction Vessel Aeration (ml/min) Enhancement by Stirrer Speed (rpm) with $0.2\mu$ Pore Air Filter Installed

| Air flux (ml/min) | Stirrer speed (rpm) (soap bubble diameter at bursting (mm)/ bursting time (sec)) | | | |
|---|---|---|---|---|
| Reading no. | 510 | 660 | 810 | 900 |
| $1^{st}$ | 0.5 (8/33) | 9.6 (24/45) | 8.4 (22/40) | 8.9 (23/43) |
| $2^{nd}$ | 0.5 (9/50) | 9.4 (24/46) | 8.7 (24/50) | 8.5 (23/45) |

TABLE 2 below lists experiment conditions and measurements made with the 50 mm diameter pre-fabricated disc membrane filter 43 removed:

TABLE 2

Reaction Vessel Aeration (ml/min) Enhancement by Stirrer Speed (rpm) without the $0.2\mu$ Pore Air Filter

| Air flux (ml/min) | Stirrer speed (rpm) (soap bubble diameter at bursting (mm)/ bursting time (sec)) | | | |
|---|---|---|---|---|
| Reading no. | 510 | 620 | 660 | 810 |
| $1^{st}$ | 0.6 (7/18) | 6.0 (20/42) | 9.6 (25/51) | 12 (26/47) |
| $2^{nd}$ | 0.8 (9/29) | 4.9 (18/37) | 8.8 (25/56) | 13 (28/53) |
| $3^{rd}$ | 0.5 (7/21) | 4.4 (17/35) | 7.9 (20/32) | 13 (27/48) |
| $4^{th}$ | — | — | 9.8 (25/50) | — |

Repeat measurements at different times and on different days showed similar intake gas flux to rpm correlation with a standard deviation of 8 to 18%. TABLES 1 and 2 of this example demonstrates without doubt that significant air flux or gas flow exchange between the new reaction vessel assembly and the ambient is possible using impeller gas pumping and compartmentalized gas bubble venting. Despite rpm increases, gas flow was restricted by the 0.2μ membrane filter 43 mounted at the gas intake at 660 rpm and beyond as suggested by data in TABLE 1. This is probably due to insufficient liquid height differential in and out of the gas-lift venting tube 50 to overcome the filter resistance to gas flow. With the micro-pore membrane filter removed, data in TABLE 2 suggest that instead impeller 22 pumping became the limiting factor to the gas flow into the vessel headspace F2 and the gas vent of gas bubbles F2b out of the gas-lift venting tube 50. Further variation of the rate of gas exchange between this reaction vessel assembly and the ambient is possible by adjusting the volume of the reaction vessel liquid phase F1, the submersion length of the gas-lift venting tube 50, i.e., the distance between the gas-lift venting tube 50's lower opening 501 and the surface of the liquid phase F1, the cross-sectional-area of the gas-lift venting tube 50's lower opening 501, and the configuring of the above contributing elements in size, geometry and relative position. For example, it is conceivable that a gas-lift venting tube 50 with a bigger diameter can produce higher gas exchange.

The present invention of reaction vessel assembly achieves enhanced aeration or gas exchange in its gas-in-liquid multiphase mixing reaction through the use of its mixing energy, and without the traditionally practiced gas sparging using external line gas under pressure. It combines the best of both shake flask and STR vessel and possesses some of the key generic features like cost and parallel experiment advantages of the traditional flasks and shaker hybrid but without their shortcomings like limited gas exchange, uncharacteristic mixing (unlike the high impeller shear and gas holdup in STR) and surface aeration. A complete invention description is not limited to what is shown and described but is susceptible to modifications and changes known to one of ordinary skill in the art.

I claim:

1. A convective flow ventilated reaction vessel assembly comprising:
    a vessel for containing a liquid phase and a gas phase;
    said gas phase is segmented into a gas intake passage and a gas venting passage, the two passages connected only at said liquid phase;
    said gas intake passage for allowing a gas to flow from outside the vessel into the gas phase in the vessel;
    a stirring means for stirring the liquid phase, and causing the gas phase in the gas intake passage to be continuously mixed into the liquid phase to form gas bubbles therein;
    said gas venting passage for allowing the gas bubbles in the liquid phase to vent from the vessel without passing through the gas phase of the gas intake passage;
    wherein the two gas passages create a net pressure differential between the gas phase in the vessel and an outside atmosphere, and wherein the pressure differential causes convective flow of a gas into and out of the vessel through the two gas passages.

2. The reaction vessel assembly of claim 1, wherein the stirring means is a motorized impeller, a magnetic stirring bar, or a shaker table attached to the vessel.

3. The reaction vessel assembly of claim 1, further comprising at least one baffle plate partially or completely submerged in the liquid phase.

4. The reaction vessel assembly of claim 1, wherein
    the vessel is a container having a top opening sealed by a head plate stopper;
    the gas intake passage is a tube inserted from the ambient through a first through-hole in the head plate stopper into the gas phase; and
    the gas venting passage is a tube inserted from the ambient through a second through-hole in the head plate stopper into the liquid phase.

5. The reaction vessel assembly of claim 4, further comprising a locking cap over the head plate stopper for holding the head plate stopper air-tight on the opening of the container.

6. The reaction vessel assembly of claim 4, wherein the stirring means is a motorized impeller held in position by an additional through-hole in the head plate stopper.

7. The reaction vessel assembly of claim 4, wherein the container is a beaker, a bottle, a flask or a carboy.

8. The reaction vessel assembly of claim 4, wherein a gas filter is provided on the gas intake passage for preventing contaminants from entering the vessel.

9. A reaction vessel array including a plurality of reaction vessel assemblies, each reaction vessel assembly comprising:
    a vessel for containing a liquid phase and a gas phase;
    said gas phase is segmented into a gas intake passage and a gas venting passage, the two passages connected only at said liquid phase;
    said gas intake passage for allowing a gas to flow from outside the vessel into the gas phase in the vessel;
    a stirring means for stirring the liquid phase, and causing the gas phase in the gas intake passage to be continuously mixed into the liquid phase to form gas bubbles in therein;
    said gas venting passage for allowing the gas bubbles in the liquid phase to vent from the vessel without passing through the gas phase of the gas intake passage;
    wherein the two gas passages create a net pressure differential between the gas phase in the vessel and an outside atmosphere, and wherein the pressure differential causes convective flow of a gas into and out of the vessel through the two gas passages.

10. The reaction vessel array of claim 9, wherein the stirring means of each reaction vessel assembly is a motorized impeller, a magnetic stirring bar, or a shaker table attached to the plurality of reaction vessel assemblies.

11. The reaction vessel array of claim 9, wherein each reaction vessel assembly further comprises at least one baffle plate partially or completely submerged in the liquid phase.

12. The reaction vessel array of claim 9, wherein for each reaction vessel assembly
    the vessel is a container having a top opening sealed by a head plate stopper;
    the gas intake passage is a tube inserted from the ambient through a first through-hole in the head plate stopper into the gas phase; and
    the gas venting passage is a tube inserted from the ambient through a second through-hole in the head plate stopper into the liquid phase.

13. The reaction vessel array of claim 12, wherein each reaction vessel assembly further comprises a locking cap over the head plate stopper for holding the head plate stopper air-tight on the opening of the container.

14. The reaction vessel array of claim 12, wherein the stirring means of each reaction vessel assembly is a motorized impeller held in position by an additional through-hole in the head plate stopper.

15. The reaction vessel array of claim 12, wherein the container of each reaction vessel assembly is a beaker, a bottle, a flask or a carboy.

16. The reaction vessel array of claim 12, wherein a gas filter is provided on the gas intake passage for each reaction vessel assembly for preventing contaminants from entering the vessel.

17. The reaction vessel array of claim 12, wherein
each reaction vessel assembly further comprises a locking cap over the head plate stopper for holding the head plate stopper air-tight on the opening of the container;
the stirring means of each reaction vessel assembly is a motorized impeller held in position by an additional through-hole in the head plate stopper;
the container of each reaction vessel assembly is a beaker, a bottle, a flask or a carboy; and
a filter is provided inside the tube used as the gas intake passage for each reaction vessel assembly for preventing contaminants from entering the vessel.

\* \* \* \* \*